United States Patent
Lim et al.

(10) Patent No.: US 7,942,905 B2
(45) Date of Patent: May 17, 2011

(54) VERTEBRAL STABILIZER

(75) Inventors: Roy Lim, Germantown, TN (US); Michael C. Sherman, Memphis, TN (US)

(73) Assignee: Warsaw Orthopedic, Inc., Warsaw, IN (US)

(*) Notice: Subject to any disclaimer, the term of this patent is extended or adjusted under 35 U.S.C. 154(b) by 960 days.

(21) Appl. No.: 11/407,642

(22) Filed: Apr. 20, 2006

(65) Prior Publication Data
US 2007/0270814 A1   Nov. 22, 2007

(51) Int. Cl.
*A61B 17/70* (2006.01)
(52) U.S. Cl. ............ 606/257; 606/53; 606/60; 606/246; 606/279; 623/17.11; 623/17.13
(58) Field of Classification Search ............ 606/257, 606/279; 267/69–72, 150; 623/17.11, 17.12, 623/17.13, 17.15
See application file for complete search history.

(56) References Cited

U.S. PATENT DOCUMENTS

| | | | | | |
|---|---|---|---|---|---|
| 1,828,383 | A | * | 10/1931 | Andersen | 188/316 |
| 3,650,498 | A | * | 3/1972 | Deak | 248/575 |
| 4,946,378 | A | * | 8/1990 | Hirayama et al. | 623/17.16 |
| 5,375,823 | A | * | 12/1994 | Navas | 623/17.15 |
| 5,961,516 | A | | 10/1999 | Graf | |
| 6,093,205 | A | * | 7/2000 | McLeod et al. | 623/17.16 |
| 6,267,764 | B1 | | 7/2001 | Elberg | |
| 6,966,910 | B2 | | 11/2005 | Ritland | |
| 6,986,771 | B2 | * | 1/2006 | Paul et al. | 606/254 |
| 2003/0055427 | A1 | * | 3/2003 | Graf | 606/61 |
| 2003/0171770 | A1 | * | 9/2003 | Kusleika et al. | 606/200 |
| 2003/0220643 | A1 | | 11/2003 | Ferree | |
| 2004/0002708 | A1 | | 1/2004 | Ritland | |
| 2004/0024460 | A1 | * | 2/2004 | Ferree | 623/17.12 |
| 2004/0049189 | A1 | | 3/2004 | Le Couedic et al. | |
| 2004/0049190 | A1 | | 3/2004 | Biedermann et al. | |
| 2004/0073215 | A1 | * | 4/2004 | Carli | 606/61 |
| 2005/0049708 | A1 | * | 3/2005 | Atkinson et al. | 623/17.16 |
| 2005/0143737 | A1 | | 6/2005 | Pafford et al. | |
| 2005/0165396 | A1 | * | 7/2005 | Fortin et al. | 606/61 |
| 2005/0182409 | A1 | | 8/2005 | Callahan et al. | |
| 2005/0203517 | A1 | | 9/2005 | Jahng et al. | |
| 2005/0261682 | A1 | * | 11/2005 | Ferree | 606/61 |
| 2005/0261685 | A1 | * | 11/2005 | Fortin et al. | 606/61 |
| 2005/0277922 | A1 | * | 12/2005 | Trieu et al. | 606/61 |
| 2005/0288670 | A1 | | 12/2005 | Panjabi et al. | |
| 2006/0084984 | A1 | * | 4/2006 | Kim | 606/61 |
| 2007/0288009 | A1 | * | 12/2007 | Brown et al. | 606/61 |
| 2008/0021459 | A1 | * | 1/2008 | Lim | 606/61 |

FOREIGN PATENT DOCUMENTS

| | | |
|---|---|---|
| EP | 0576379 A1 | 12/1993 |
| EP | 1388323 A1 | 2/2004 |

OTHER PUBLICATIONS

European Patent Office, International Searching Authority, Notification of Transmittal of the International Search report and the Written Opinion of the International Searching Authority or the Declaration, International Application No. PCT/US2007/065947, Sep. 5, 2007, 11 pages.

* cited by examiner

*Primary Examiner* — Eduardo C Robert
*Assistant Examiner* — Christian Sevilla

(57) ABSTRACT

A system for flexibly stabilizing a vertebral motion segment by connecting a first vertebra and a second vertebra is disclosed. The system includes a bumper with a resilient central member. The system is designed such that the resilient central member is compressed in both compression and extension of the bumper or vertebral motion segment. The system includes first and second means for connecting the bumper to the vertebrae.

27 Claims, 9 Drawing Sheets

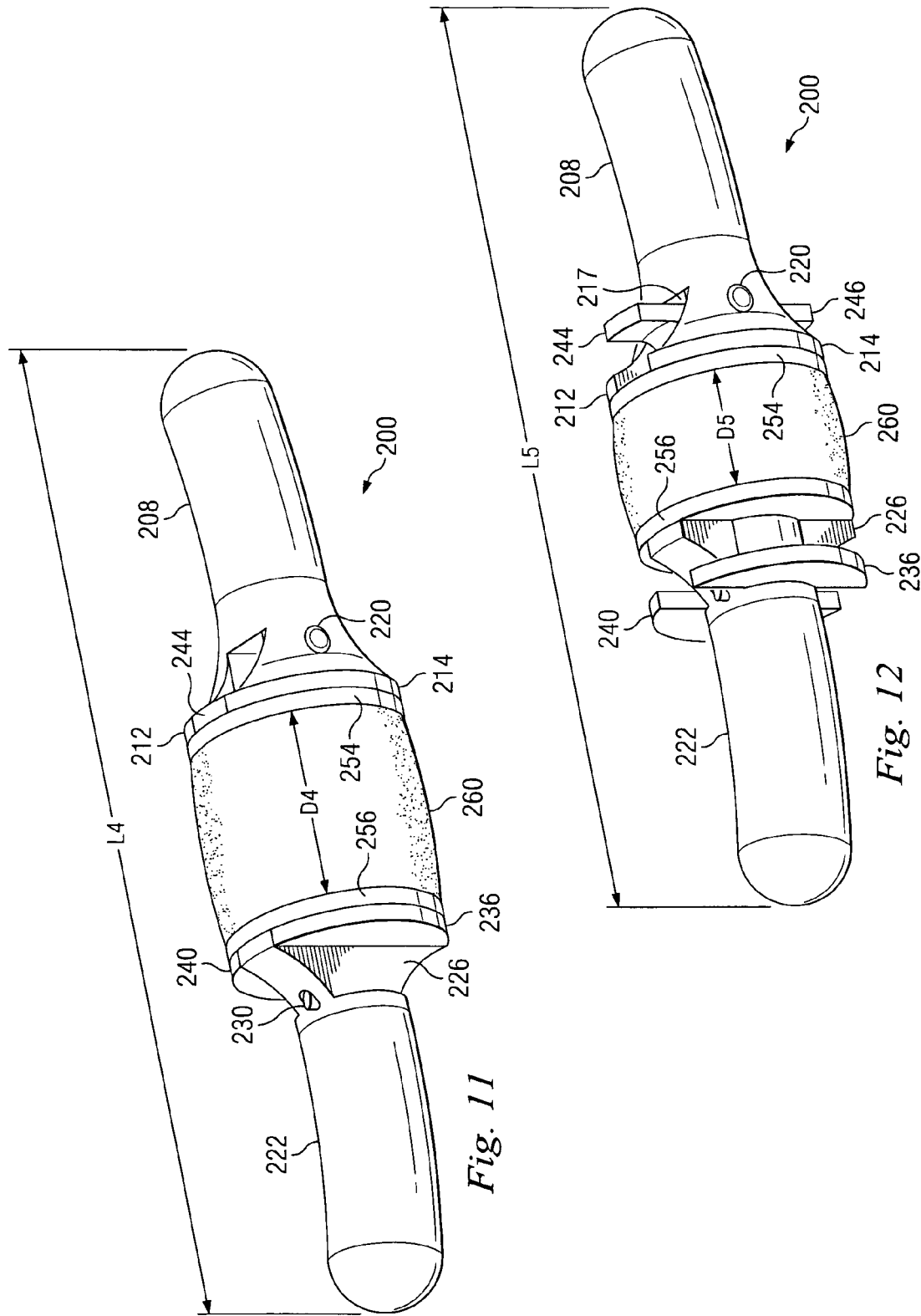

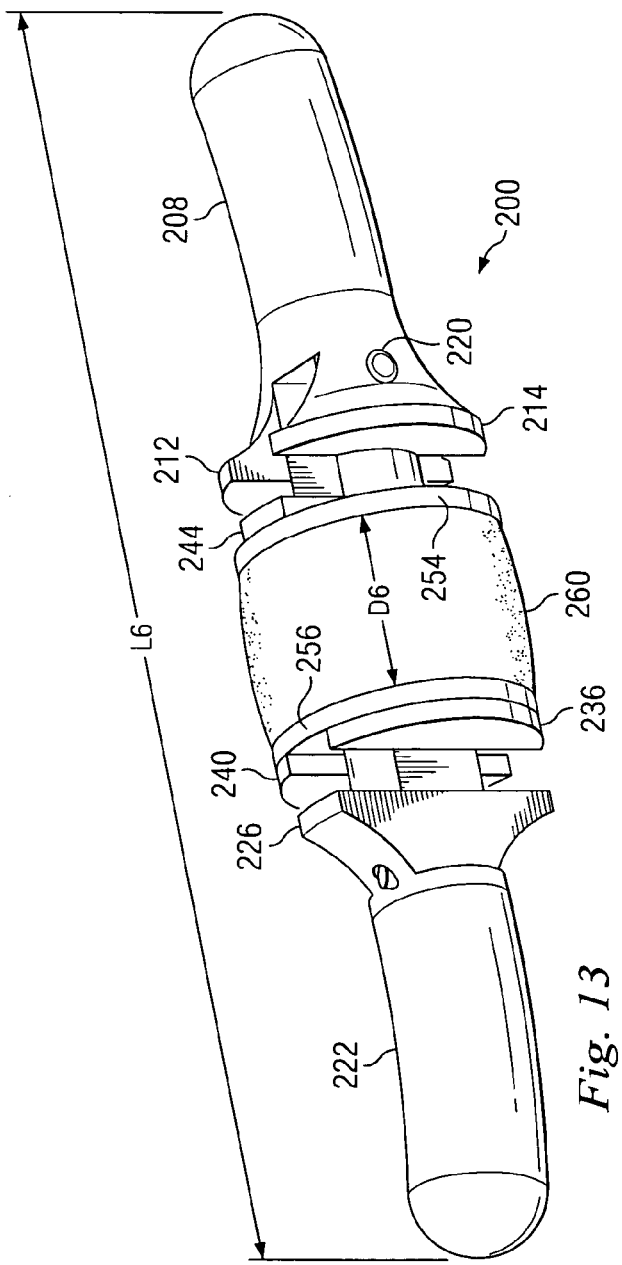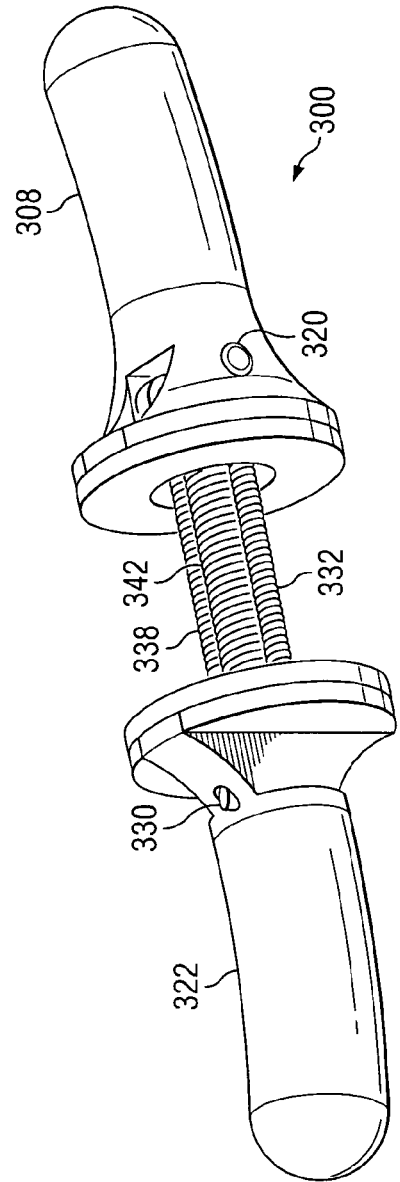
Fig. 13
Fig. 14

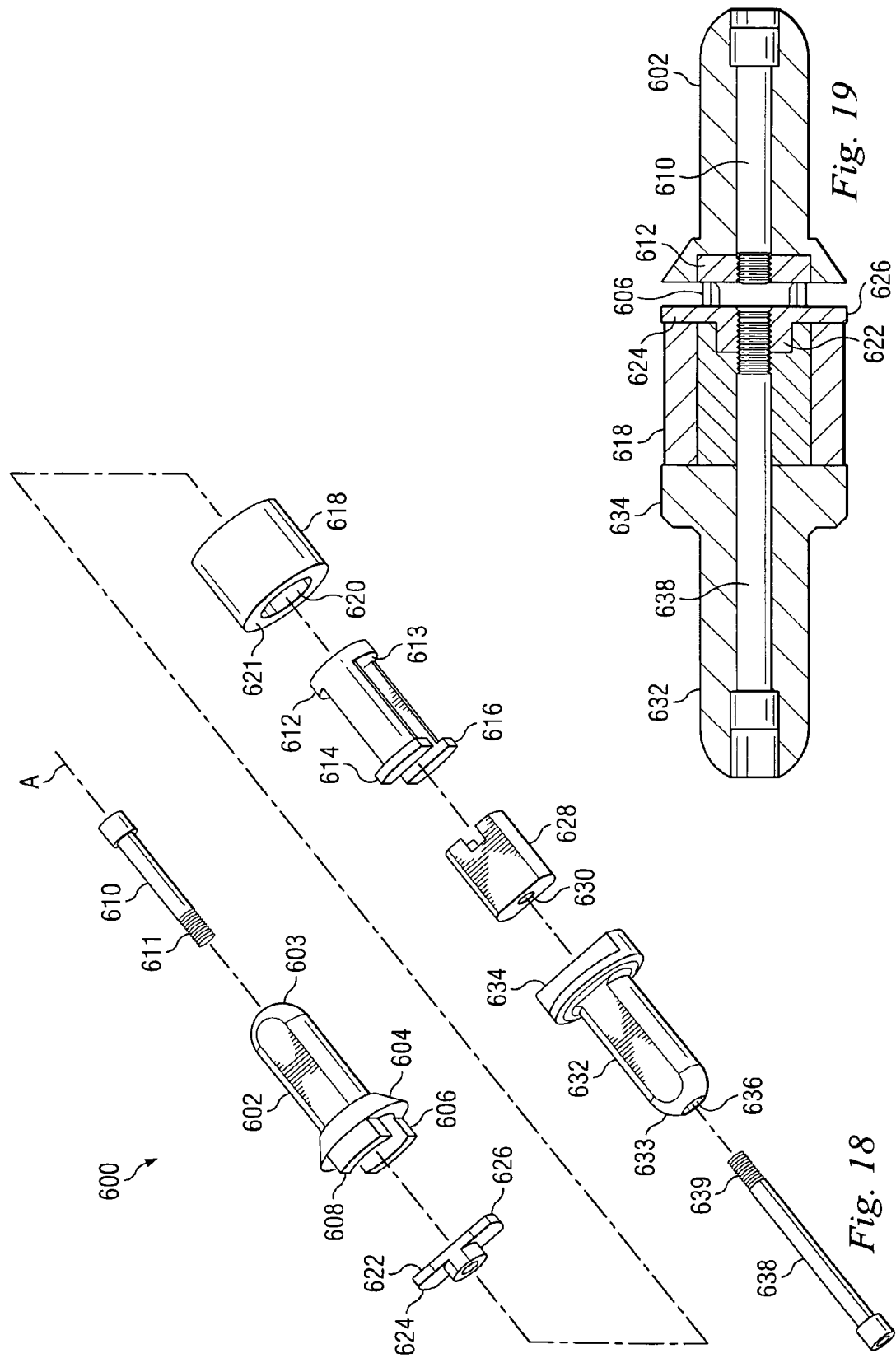

VERTEBRAL STABILIZER

BACKGROUND

Severe back pain and nerve damage may be caused by injured, degraded, or diseased spinal motion segments and particularly, spinal discs. Current methods of treating these damaged spinal discs may include vertebral fusion, nucleus replacements, or motion preservation disc prostheses. Disc deterioration and other spinal deterioration is painful in of itself and may cause spinal stenosis, a narrowing of the spinal canal and/or the intervertebral foramen, that causes pinching of the spinal cord and associated nerves. Current methods of treating spinal stenosis include laminectomy or facet resection. Alternative and potentially less invasive options are needed to provide spinal pain relief.

SUMMARY

In one aspect, the present disclosure is directed to a device for dynamically stabilizing a vertebral motion segment.

In another aspect, this disclosure is directed to a method of flexibly stabilizing a joint. The method comprises providing a dynamic device adapted to compress a flexible member during both compression and extension of the dynamic device, securing a first portion of the dynamic device to a first bony portion of the joint, and securing a second portion of the dynamic device to a second bony portion of the joint.

In yet another aspect, the disclosure provides an apparatus for dynamically stabilizing a vertebral motion segment. The apparatus includes a first attachment portion, a second attachment portion, a resilient member, and a means for coupling the first and second attachment portions to the resilient member to convert both compressive and tensile forces applied across the first and second attachment portions to a compressive force upon the resilient member.

These and other aspects, forms, objects, features, and benefits of the present invention will become apparent from the following detailed drawings and descriptions.

BRIEF DESCRIPTION OF THE DRAWINGS

FIG. 11 is a perspective view of a bumper according to another aspect of the present disclosure.

FIG. 12 is a perspective view of the bumper of FIG. 11 in a compressed position.

FIG. 13 is a perspective view of the bumper of FIG. 11 in an extended position.

FIG. 14 is a perspective view of a portion of a bumper according to another aspect of the present disclosure.

FIG. 18 is a perspective exploded view of a vertebral stabilizer according to another aspect of the present disclosure.

FIG. 19 is a side cross-sectional view of the vertebral stabilizer of FIG. 18 when assembled.

DETAILED DESCRIPTION

Figure 1:
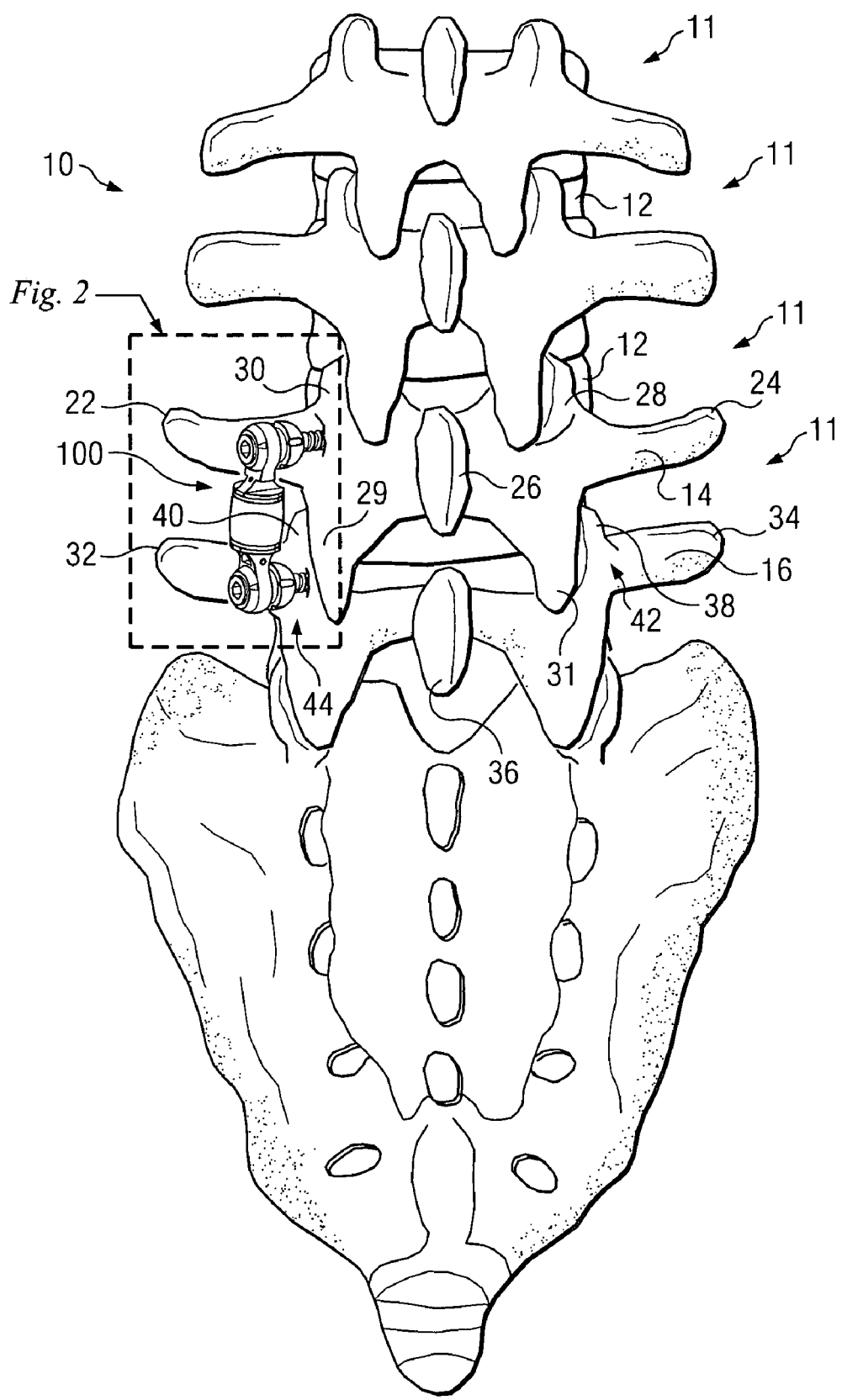
FIG. 1 is a posterior view of a vertebral column with a vertebral stabilizing system according to one embodiment of the present disclosure.

The present disclosure relates generally to the field of orthopedic surgery, and more particularly to systems and methods for stabilizing a spinal motion segment. For the purposes of promoting an understanding of the principles of the invention, reference will now be made to embodiments or examples illustrated in the drawings, and specific language will be used to describe the same. It will nevertheless be understood that no limitation of the scope of the invention is thereby intended. Any alteration and further modifications in the described embodiments, and any further applications of the principles of the invention as described herein are contemplated as would normally occur to one skilled in the art to which the disclosure relates.

Referring to FIG. 1, the numeral 10 refers to a spinal column having a series of vertebral motion segments 11, each including an intervertebral disc 12 and two facet joints 42, 44. One of the vertebral motion segments 11 will be described further with reference to adjacent vertebrae 14, 16. The vertebra 14 includes transverse processes 22, 24; a spinous process 26; superior articular processes 28, 30; and inferior articular processes 29, 31. Similarly, the vertebra 16 includes transverse processes 32, 34; a spinous process 36; superior articular processes 38, 40; and inferior articular processes (not labeled). Although the illustration of FIG. 1 generally depicts the vertebral motion segment 11 as a lumbar vertebral motion segment, it is understood that the devices, systems, and methods of this disclosure may also be applied to all regions of the vertebral column, including the cervical and thoracic regions. Furthermore, the devices, systems, and methods of this disclosure may be used in non-spinal orthopedic applications.

A facet joint 42 is formed, in part, by the adjacent articular processes 29, 38. Likewise, another facet joint 44 is formed, in part, by the adjacent articular processes 31, 40. Facet joints also may be referred to as zygapophyseal joints. A healthy facet joint includes a facet capsule extending between the adjacent articular processes. The facet capsule contains cartilage and synovial fluid to permit the articulating surfaces of the articular processes to remain lubricated and glide over one another. The type of motion permitted by the facet joints is dependent on the region of the vertebral column. For example, in a healthy lumbar region, the facet joints limit rotational motion but permit greater freedom for flexion, extension, and lateral bending motions. By contrast, in a healthy cervical region of the vertebral column, the facet joints permit rotational motion as well as flexion, extension, and lateral bending motions. As the facet joint deteriorates, the facet capsule may become thickened, compressed, and worn, losing its ability to provide a smooth, lubricated interface between the articular surfaces of the articular processes.

This may cause arthritic pain and limit motion at the affected motion segment. Facet joint deterioration may also cause inflammation and enlargement of the facet joint which may, in turn, contribute to spinal stenosis. Removal of an afflicted articular process may result in abnormal motions and loading on the remaining components of the motion segment. The embodiments described below may be used to stabilize a deteriorated motion segment while still allowing some level of natural motion.

Injury, disease, and deterioration of the intervertebral disc 12 may also cause pain and limit motion. In a healthy intervertebral motion segment, the intervertebral disc permits rotation, lateral bending, flexion, and extension motions. As the intervertebral motion segment deteriorates, the intervertebral disc may become compressed, displaced, or herniated, resulting in excess pressure in other areas of the spine, particularly the posterior bony elements of the afflicted vertebrae. This deterioration may lead to spinal stenosis. The embodiments described below may restore more natural spacing to the posterior bony elements of the vertebrae, decompress an intervertebral disc, and/or may relieve spinal stenosis. Referring still to FIG. 1, in one embodiment, a vertebral stabilizing system 100 may be used to provide support to the vertebrae 14, 16, decompress the disc 12 and the facet joint 44, and/or relieve stenosis.

Figure 2:
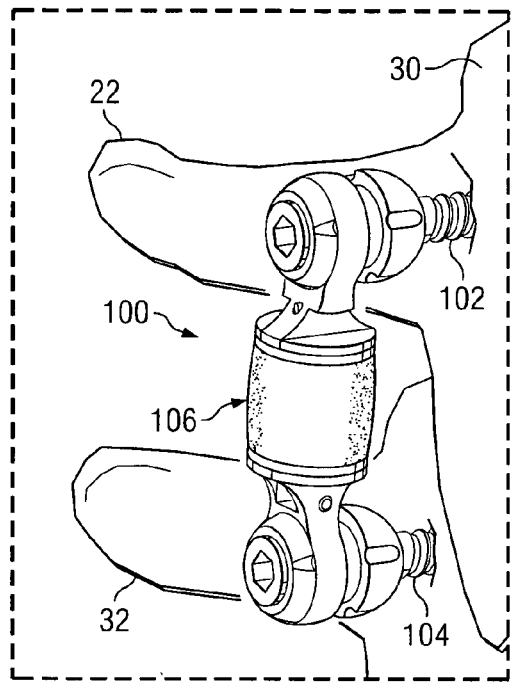
FIG. 2 is a close-up view of the vertebral stabilizing system of FIG. 1.
Figure 3:
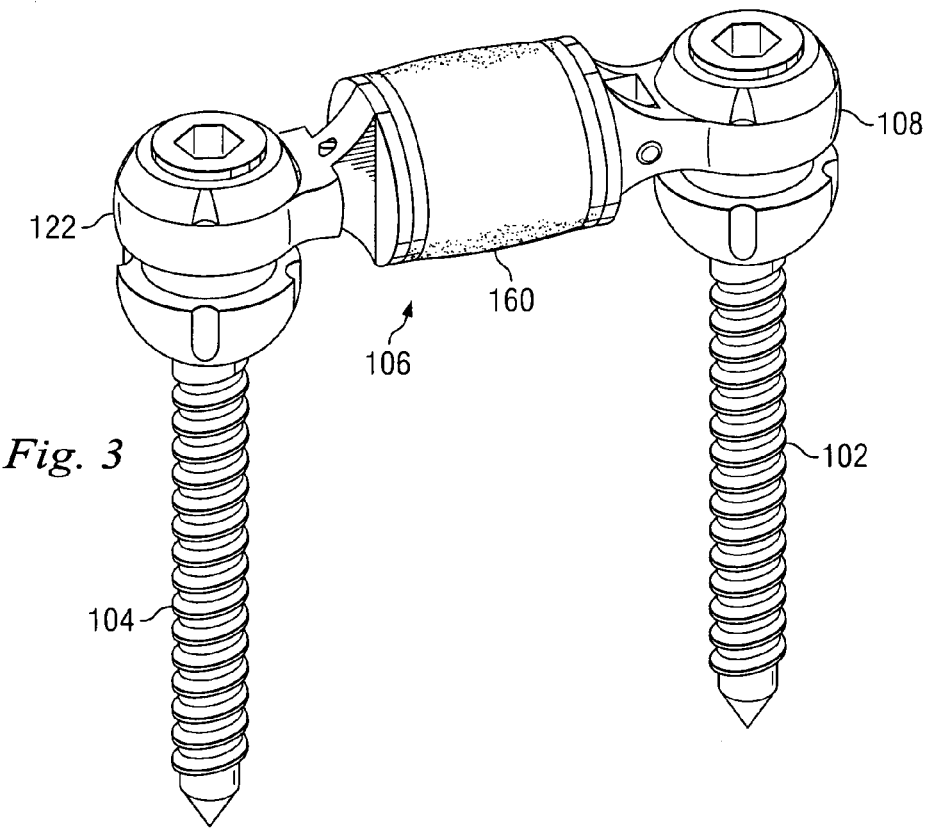
FIG. 3 is a perspective view of a vertebral stabilizing system according to one aspect of the present disclosure.
Figure 4:
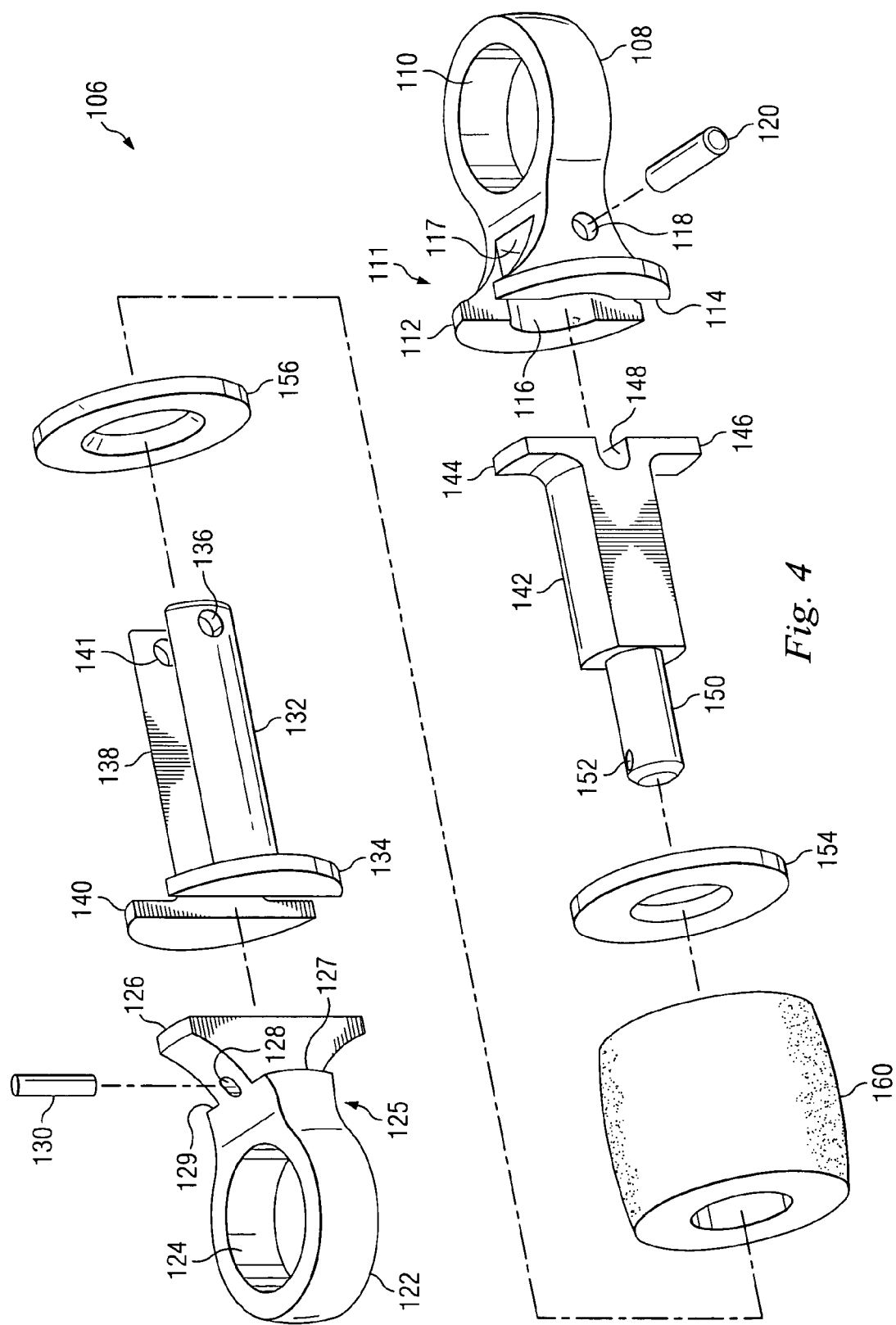
FIG. 4 is an exploded view of a portion of the vertebral stabilizing system of FIG. 3.

FIGS. 2-4 show the vertebral stabilizing system 100 disclosed in FIG. 1 in greater detail. FIGS. 2 and 3 show the system 100 assembled. As shown in FIGS. 2 and 3, the vertebral stabilizing system 100 includes a superior vertebral attachment member 102, an inferior vertebral attachment member 104, and a damper or bumper 106. FIG. 4 shows the bumper 106 of the system 100 in an exploded state.

The bumper 106 is attached at each end to the attachment members 102, 104 that are engaged with the spine. There are multiple ways the bumper 106 can be connected to the attachment members 102, 104. The precise means of connecting the bumper 106 and attachment members 102, 104 will vary depending on the specific embodiments of the bumper and attachment members being used. In some embodiments, the connection will facilitate at least a limited amount of movement between the bumper 106 and the attachment members. FIGS. 1-3 illustrate one means of connection: utilizing a ball-and-socket connection of a multi-axial screw. Other examples of connection means will be described in relation to other embodiments below. However, the examples provided are not intended to be an exhaustive list. Other connection means, such as fixed angle screws, that would be recognized by a person having ordinary skill in the art are understood to be included in the present disclosure.

The bumper 106 provides compressive support and load distribution to relieve the intervertebral disc 12. In addition, in some embodiments the bumper 106 dampens the forces on the intervertebral disc 12 and facet joint 44 during vertebral motion. Accordingly, in some aspects the bumper 106 assists during bending, compression, or extension, to provide a flexible dampening force to limit the chance of overcompression or overextension when the surrounding muscles or ligaments are weak. Further, in some embodiments the bumper 106 allows torsional movement of the vertebrae 14 relative to the vertebrae 16.

Referring to FIG. 4, the bumper 106 includes a superior attachment portion 108 adapted to facilitate connection of the bumper to the superior attachment member 102. The superior attachment portion 108 includes an opening 110 adapted to movably engage a protrusion or protrusions of the superior attachment member 102. The bumper 106 also includes an inferior attachment portion 122 adapted to facilitate connection of the bumper to the inferior attachment member 104. The inferior attachment portion 122 is substantially similar to the superior attachment portion 108. The inferior attachment portion includes an opening 124 adapted to movably engage a protrusion or protrusions of the inferior attachment member 104. Though illustrated as being substantially similar in the current embodiment, it is not necessary for the attachment portions 108, 122 for connecting to the attachment members 102, 104, respectively, to be the same.

Connected to and extending from the superior attachment portion 108 is an engagement portion 111. The engagement portion 111 includes flanges 112, 114. The function of flanges 112, 114 will be described in greater detail below. The engagement portion 111 also includes an opening 116. The opening 116 is adapted to receive other components of the bumper 106, as described below. Further, in some embodiments the engagement portion 111 includes abutment surface 117 to limit the compression of the bumper 106, as described below. The engagement portion 111 also includes opening 118 adapted to receive locking pin 120. In the illustrated embodiment, the attachment portion 108 and engagement portion 111 are integrally formed from a single piece of material.

Similarly, connected to and extending from the inferior attachment portion 122 is an engagement portion 125. The engagement portion 125 includes a flange 126. The flange 126 includes an opening (not shown) adapted to receive a portion of another component of the bumper 106, as described below. Again, the function of flange 126 will described in greater detail below. The engagement portion 125 may also include abutments 127, 129 that may serve to limit the compression of the bumper 106, as described below. The engagement portion 125 also includes an opening 128 adapted to receive locking pin 130.

Figure 5:
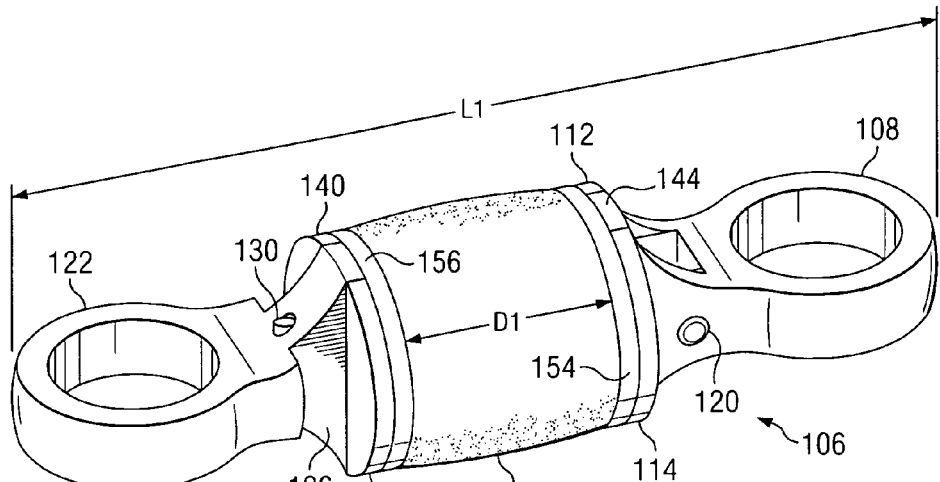
FIG. 5 is a perspective view of a portion of the vertebral stabilizing system of FIG. 3 in a neutral position.
Figure 6:
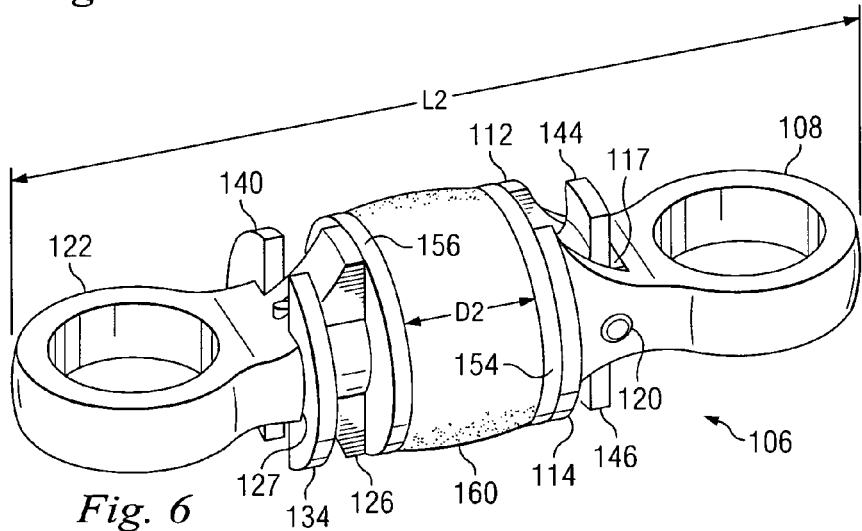
FIG. 6 is a perspective view of a portion of the vertebral stabilizing system of FIG. 3 in a compressed position.
Figure 7:
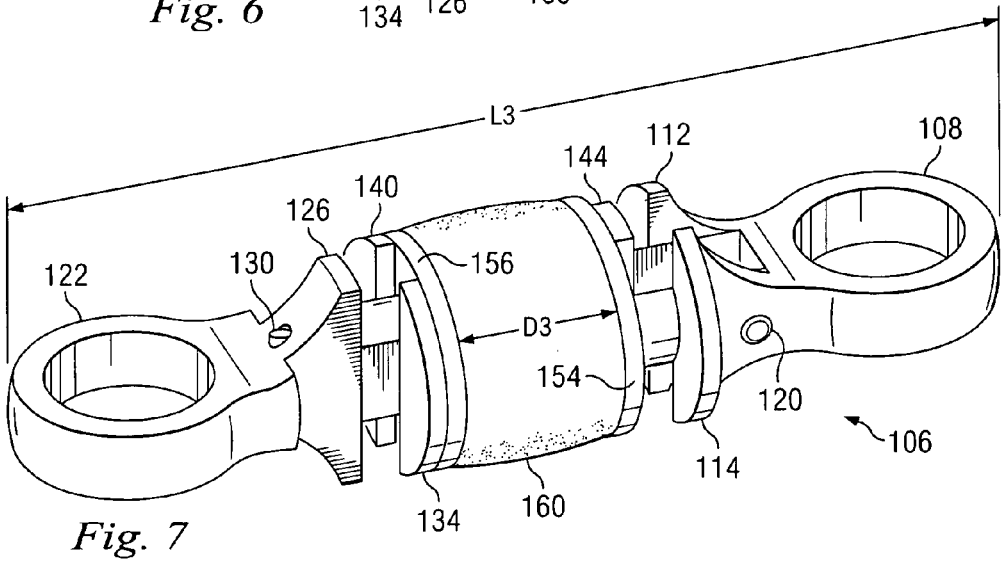
FIG. 7 is a perspective view of a portion of the vertebral stabilizing system of FIG. 3 in an extended position.

Referring now to FIGS. 4 and 8-10, the bumper 106 includes outer rods 132, 138. As illustrated, the outer rod 132 includes a flange portion 134 and an opening 136. Similarly, outer rod 138 includes a flange portion 140 and an opening 141 (see FIG. 8). The outer rods 132, 138 are adapted to fit into opening 116 of the engagement portion 111. Further, the openings 136, 141 of the outer rods 132, 138 are adapted to receive locking pin 120. Thus, when the bumper 106 is fully assembled—as shown in FIGS. 5-7—a portion of the outer rods 132, 138 will be disposed within the opening 116 and the outer rods 132, 138 will be connected to the engagement portion 111 by the locking pin 120. The locking pin 120 may be replaced by any other device capable of securing the outer rods 132, 138 to the engagement portion 111. In other embodiments, the outer rods 132, 138 and the engagement portion 111 are a monolithic structure. That is, the outer rods 132, 138 and the engagement portion 111 are a single piece such that they need not be connected using a locking pin or any other mechanism.

The bumper 106 also includes an inner rod 142. At one end, the inner rod 142 includes flanges 144, 146 and a notch 148. The notch 148 is sized such that the locking pin 120 may fit within the notch. At the other end, the inner rod 142 includes a protrusion 150. The protrusion 150 is adapted to pass into the opening (not shown) of flange 126 when the bumper 106 is assembled. The protrusion 150 includes an opening 152 adapted to receive locking pin 130. Thus, when the bumper 106 is assembled—as shown in FIGS. 5-7—the inner rod 142 will be connected to engagement portion 125 by the locking pin 130. The locking pin 130 may be replaced by any other device capable of securing the inner rod 142 to the engagement portion 125. In other embodiments, the inner rod 142 and the engagement portion 125 may be a monolithic structure. That is, the inner rod 142 and the engagement portion 125 may be a single piece such that they need not be connected using a locking pin or any other mechanism.

The bumper 106 also includes washers 154, 156 and a central member 160. The washers 154, 156 and the central member 160 include openings that form a passage the outer rods 132, 138 and inner rod 142 may pass through. In the current embodiment, the outer rods 132, 138 are adapted to be positioned on either side of the inner rod 142, as shown best in FIG. 8. As will be described in greater detail below, the washers 154, 156 are utilized to more evenly distribute the compressive force from the flanges 112, 114, 126, 134, 140, 144, and 146 to the central member 160 over a substantial portion of the end surfaces of the resilient central member. In other embodiments, washers are not included and the flanges are adapted to directly contact the central member 160.

Figure 16:
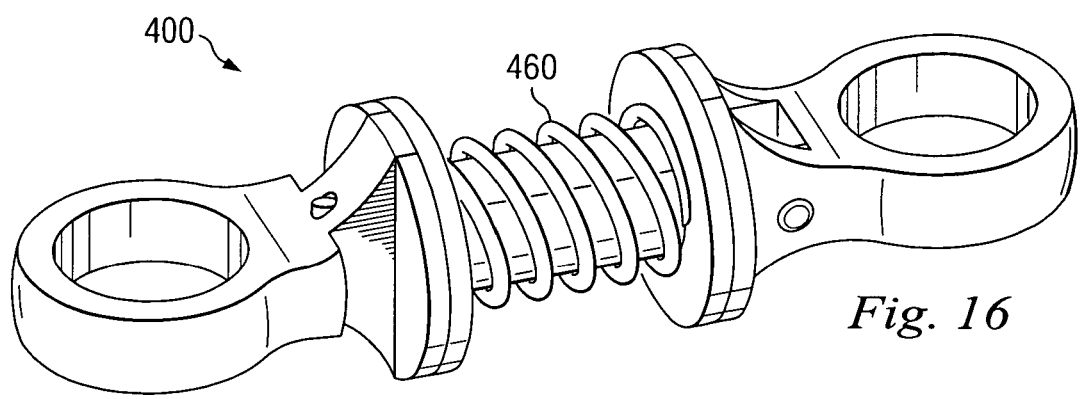
FIG. 16 is a perspective view of a portion of a bumper according to another aspect of the present disclosure.
Figure 17:
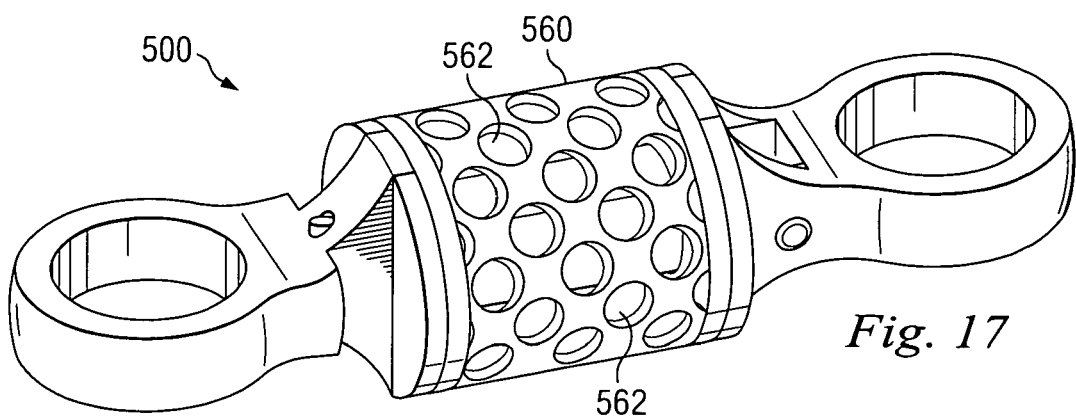
FIG. 17 is a perspective view of a bumper according to another aspect of the present disclosure.

The bumper 106 functions such that the central member 160 is compressed whether the attachment portions 108, 122 are compressed towards or extended away from each other. To this end the central member 160 may take various forms. For example, the resilient central member 160 may be formed from any suitable material such as silicon, polycarbonate, urethane, shape memory alloys, polyetheretherketone ("PEEK"), resorbable materials, spring steels, coil springs, or other suitable materials. The central member 160 may also include various features such as slots or perforations to facilitate flexibility; a resorbable sleeve to facilitate a delay of several days, weeks, or months before the bumper becomes active; a spring; a piston; a pneumatic mechanism; a hydraulic mechanism; or other features as would be apparent to one skilled in the art. FIGS. 16 and 17, described below, show alternative exemplary embodiments of a central member.

The other components of the bumper 106, such as the attachment portions 108, 122, the engagement portions 111, 125, and the inner and outer rods 142, 132, 138, may be formed from any suitable biocompatible material including metals, ceramics, polymers, and combinations thereof. For example, in one aspect metals such as cobalt-chromium alloys, titanium alloys, nickel titanium alloys, or stainless steel alloys. Also, ceramic materials such as aluminum oxide or alumina, zirconium oxide or zirconia, compact of particulate diamond, or pyrolytic carbon are suitable in some aspects. Further, in some aspects polymer materials, including any member of the polyaryletherketone (PAEK) family such as polyetheretherketone (PEEK), carbon-reinforced PEEK, or polyetherketoneketone (PEKK); polysulfone; polyetherimide; polyimide; ultra-high molecular weight polyethylene (UHMWPE); or cross-linked UHMWPE, are used. Finally, different portions of the bumper 106 may be formed of different materials, permitting metal on metal, metal on ceramic, metal on polymer, ceramic on ceramic, ceramic on polymer, or polymer on polymer constructions.

FIGS. 5-7 show the bumper 106 in various stages of neutrality, compression, and extension. FIG. 5 shows the bumper 106 in a neutral position. In the neutral position, the bumper 106 length has a length L1 extending between the outer edges of the attachment portions 108, 122. Also, while in the neutral position the central member 160 has a length D1. Further, in a neutral position the proximal flanges 112, 114 of attachment portion 108 are in substantial alignment with distal flanges 144, 146 of attachment portion 122 and proximal flange 126 of attachment portion 122 is in substantial alignment with distal flanges 134, 140 of attachment portion 108, as shown.

As shown in FIG. 6, during compression of the bumper 106 the flanges 112, 114 engage washer 154 and the flange 126 engages washer 156 to compress the central member 160, while the flanges 134, 140, 144, 146 extend away from the washers and central member. In compression, the bumper 106 has a length L2 extending between the outer edges of the attachment portions 108, 122. The length L2 is less than the length L1. Further, in compression the central member 160 has a length D2 that is less than length D1. In some embodiments, the amount of compression may be limited by the flanges 134, 140 contacting the abutments 127, 129 of the engagement portion 125. Similarly, in some embodiments the amount of compression may be limited by the flanges 144, 146 contacting the abutment surface 117 and/or notch 148 engaging locking pin 120.

As shown in FIG. 7, during extension of the bumper 106 the flanges 144, 146 engage washer 154 and the flanges 134, 140 engage washer 156 to compress the central member 160, while flanges 112, 114, and 126 extend away from the washers and central member. In extension, the bumper 106 has a length L3 extending between the outer edges of the attachment portions 108, 122. The length L3 is greater than the length L1. Further, in extension the central member 160 has a length D3 that is less than length D1. Thus, in either extension or compression the central member 160 is compressed. Though not shown in the current embodiment, in other embodiments the bumper 106 includes a feature or features similar to the abutments 117, 127, 129 to limit the amount of extension.

Figure 8:
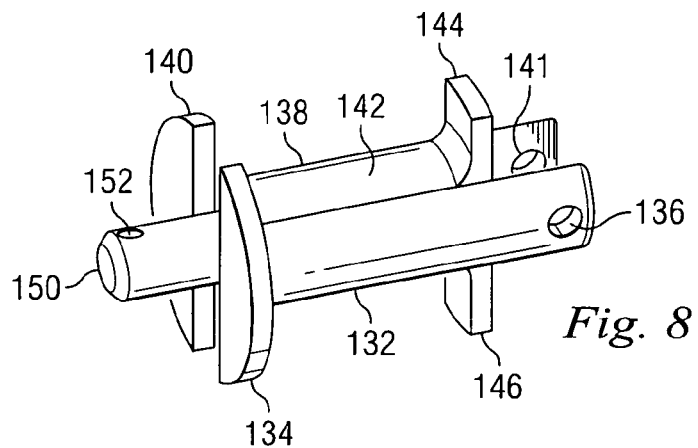
FIG. 8 is a perspective view of a portion of the vertebral stabilizing system of FIG. 3.
Figure 9:
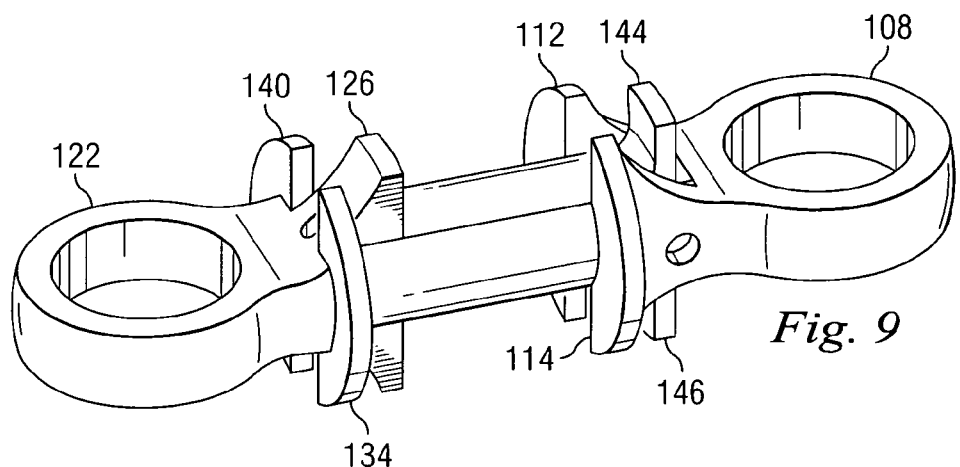
FIG. 9 is a perspective view of a portion of the vertebral stabilizing system of FIG. 3 in a compressed position.
Figure 10:
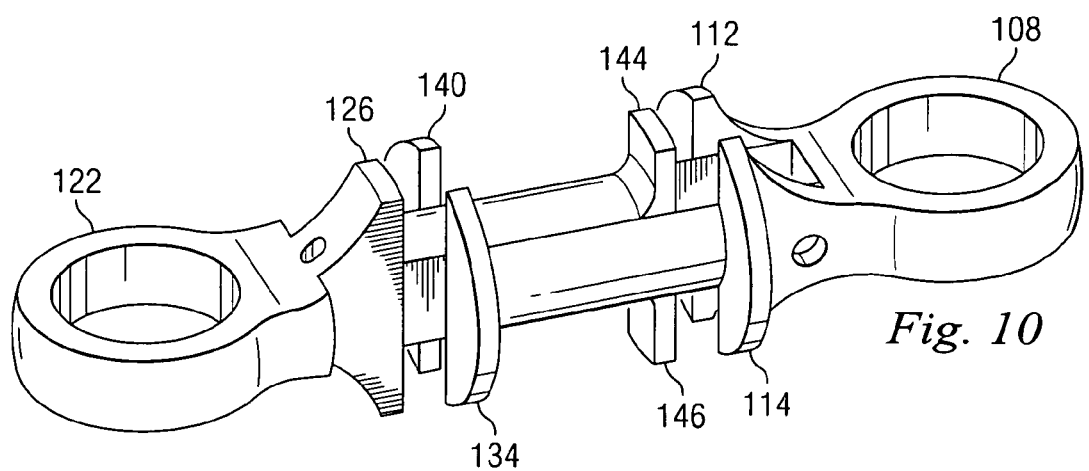
FIG. 10 is a perspective view of a portion of the vertebral stabilizing system of FIG. 3 in an extended position.

FIGS. 8-10 show more clearly the inner workings of the bumper 106. FIG. 8 illustrates the orientation of the outer rods 132, 138 to the inner rod 142 in a double shear configuration. During compression or a decrease in length, the flanges 144, 146, 134, 140 of the inner and outer rods 142, 132, 138 extend outwardly away from the central member 160. Simultaneously, the flanges 112, 114, 126 of the engagement portions 111, 125 move inwardly, compressing the central member 160. FIG. 9 shows the bumper 106 without the central member in a compressed state. During extension or an increase in length, the flanges 112, 114, 126 of the engagement portions 111, 125 extend outwardly away from the central member 160. Simultaneously, the flanges 144, 146, 134, 140 of the inner and outer rods 142, 132, 138 move inwardly, compressing the central member 160. FIG. 10 shows the bumper 106 without the central member in an extended state.

FIGS. 11-13 show a damper 200 according to another embodiment of the present disclosure. Damper 200 may be substantially similar to bumper 106 described above. However, the damper 200 includes attachment portions 208, 222 that are rods or elongated members that are joined to the spine via conventional fixation devices (not shown). As shown, the attachment portions 208, 222 may be pre-bent. The attachment portions 208, 222 may be pre-bent to match the curvature of a spinal rod system or other attachment means. In other embodiments the attachment portions 208, 222 are adapted to directly engage the vertebrae.

The damper 200 functions in a substantially similar manner as bumper 106. Thus, the orientation of the inner and outer rods and the flanges of damper 200 is substantially similar to the orientation of the inner and outer rods and the flanges of bumper 106. For this reason, a detailed description of the mechanical structure of damper 200 will not be made. However, the functionality of damper 200 will now be explained.

FIGS. 11-13 show the damper 200 in various stages of neutrality, compression, and extension. FIG. 11 shows the damper 200 in a neutral position. In the neutral position, the damper 200 length has a length L4 extending between the outer edges of the attachment portions 208, 222. Also, while in the neutral position the central member 260 has a length D4. Further, in a neutral position the flanges 212, 214 are in substantial alignment with flanges 244, 246 and flange 226 is in substantial alignment with flanges 234, 240, as shown.

As shown in FIG. 12, during compression of the damper 200 the flanges 212, 214 engage washer 254 and the flange 226 engages washer 256 to compress the central member 260, while the flanges 234, 240, 244, 246 extend away from the washers and central member. In compression, the damper 200 has a length L5 extending between the outer edges of the attachment portions 208, 222. The length L5 is less than the length L4. Further, in compression the central member 260 has a length D5 that is less than length D4. In some embodiments, the amount of compression may be limited by the flanges 234, 240, 244, 246 contacting abutments of the engagement portions.

As shown in FIG. 13, during extension of the damper 200 the flanges 244, 246 engage washer 254 and the flanges 234, 240 engage washer 256 to compress the central member 260, while flanges 212, 214, and 226 extend away from the washers and central member. In extension, the damper 200 has a length L6 extending between the outer edges of the attachment portions 208, 222. The length L6 is greater than the length L4. Further, in extension the central member 160 has a length D6 that is less than length D4. Thus, in either extension or compression the central member 160 is compressed. Though not shown in the current embodiment, in other embodiments the damper 200 includes a feature or features to limit the amount of extension.

Figure 15:
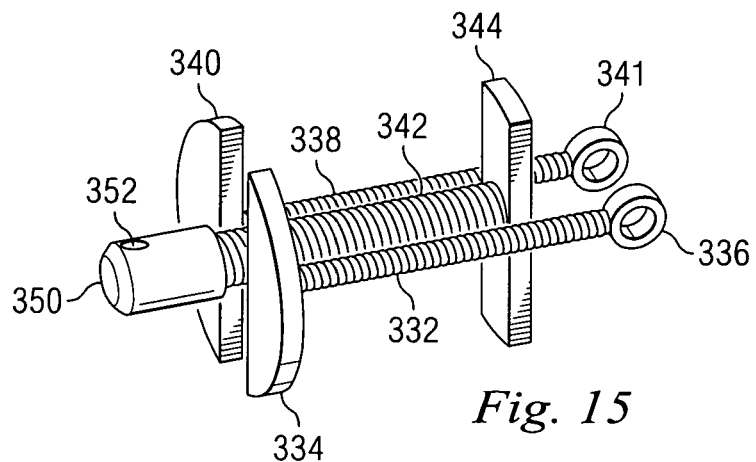
FIG. 15 is a perspective view of part of the portion of a bumper of FIG. 14.

FIG. 14 shows a portion of a bumper 300 according to another embodiment of the present disclosure. Bumper 300 may be substantially similar to bumper 106 and damper 200 described above. The bumper 300 includes attachment portions 308, 322 similar to bumper 200. Bumper 300 includes outer rods 332, 338 and an inner rod 342 that are flexible. It should be noted that the inner and outer rods of bumper 106 and damper 200 are also flexible in some embodiments. The inner and outer rods 342, 332, 338 are shown in greater detail in FIG. 15.

The outer rod 332 includes a flange 334 at one end and an opening 336 at the other. Similarly, the outer rod 338 includes a flange 340 at one end and an opening 341 at the other. The openings 336, 341 are adapted to receive locking pin 320. The inner rod 342 includes a flange 344 at one end and an extension 350 at the other. The extension 350 includes an opening 352 adapted to receive locking pin 330. As shown, the orientation of the outer rods 332, 338 to the inner rod 342 is substantially similar to those of the embodiments described above. However, the inner and outer rods 342, 332, 338 are flexible. That is, the inner and outer rods 342, 332, 338 allow at least some bending along their length. In this way, the bumper 300 allows at least some transverse movement or flexion along the length of the bumper in addition to compression and extension. The inner and outer rods 342, 332, 338 may be cables, flexible rods, or other flexible components constructed of any suitable material, including braided steel, cobalt-chrome, cobalt-chrome alloys, titanium, and titanium alloys (such as Ti64 and Nitinol). In addition, the flexible rod could be formed from a polymer braided construction, such as Polyethylene terephthalate ("PET"), UHMWPE, or Spectra.

The central member (not shown) of bumper 300 may be substantially similar to other central members described in the present disclosure. In some embodiments, the central member of bumper 300 is also flexible in a direction transverse to the length of the bumper. Further, in some embodiments, the central member may serve to limit or dampen the amount of transverse movement. For example, in some embodiments the central member may include a rigid outside shell with a malleable core. In such an embodiment, the malleable core would allow some transverse motion of the inner and outer rods 342, 332, 338, but the rigid outside shell would serve to limit the extent of the transverse motion. In some embodiments, the rigid outside shell is utilized to limit the amount of extension and compression in addition to, or in place of, limiting transverse motion.

The bumper 300 functions in a substantially similar manner to bumper 106 and damper 200 described above and, therefore, will not be described in detail. However, it should be noted that the bumper 300 functions so that in both extension and compression the central member (not shown) is compressed.

FIG. 16 shows a vertebral stabilizer 400 according to another embodiment of the present disclosure. The stabilizer 400 may be substantially similar to bumper 106, damper 200, and bumper 300 described above. The vertebral stabilizer 400 includes a central member 460 that is a spring. In some embodiments, the central member 460 is biased towards compression or extension according to the patient's symptoms. Further, in some embodiments the central member 460 is formed from a shape-memory allow, such as nitinol. In another aspect, the central member 460 is a variable rate spring such that the opposition to movement increases as the change in length increases. That is, as the vertebral stabilizer 400 moves further from a neutral position, the greater the resistance provided by the central member 460. This increasing resistance is not limited to embodiments employing a spring as the central member 460. Rather, other types of central members may exhibit similar characteristics.

FIG. 17 shows a bumper 500 according to another embodiment of the present disclosure. Again, the bumper 500 may be substantially similar to bumper 106, damper 200, bumper 300, and vertebral stabilizer 400 described above. The bumper 500 includes a central member 560 that includes a plurality of perforations or openings 562. The perforations 562 serve to reduce the stiffness of the central member 560, allowing greater flexibility for the bumper 500. Other types of openings or geometries are utilized in other embodiments to reduce the stiffness of the central member 560 and bumper 500 as a whole.

FIGS. 18 and 19 show a vertebral stabilizer 600 according to another embodiment of the present disclosure. The vertebral stabilizer 600 includes a superior attachment portion 602 adapted to facilitate connection of the vertebral stabilizer to a superior vertebra. The superior attachment portion 602 includes a superior engagement portion 604 having flanges 606, 608. The superior attachment portion 602 also includes a passage (not shown) adapted to receive a securing device 610. The passage is configured such that the securing device 610 may pass through the superior attachment portion 602 along a longitudinal axis A of the vertebral stabilizer 600 and engage the superior attachment portion 602 to a inner portion 612. The inner portion 612 includes flanges 614, 616.

As shown, the securing device 610 includes a threaded portion 611 adapted to mate with a portion of the inner portion 612. However, any suitable means of securing the superior attachment portion 602 to the inner portion 612 may be utilized. Further the securing device 610 may be sized such that the securing device is recessed with respect to a superior end 603 of the superior attachment portion 602 when the superior attachment portion is secured to the inner portion 612. As shown in FIG. 19, the securing device 610 engages a shoulder portion of the opening in the superior attachment portion 602 to limit how far into the opening the securing device may travel. A resilient body 618 includes an opening 620 and a surface 621. The opening 620 is adapted to receive inner portion 612 such that flanges 614, 616 may engage the surface 621.

The vertebral stabilizer 600 also includes an inferior attachment portion 632 adapted to facilitate connection of the vertebral stabilizer to an inferior vertebra. The inferior attachment portion 632 includes an inferior engagement flange portion 634. The inferior attachment portion 632 also includes a passage 636 adapted to receive a securing device 638. The passage is configured such that the securing device 638 may pass through the inferior attachment portion 632 along the longitudinal axis A of the vertebral stabilizer 600, through a passage 630 of an intermediate piece 628, and engage the inferior attachment portion 632 to the flange piece 622. The flange piece 622 includes flanges 624, 626. The flange piece 622 is adapted for placement between the resilient body 618 and the inner portion 612 such that flanges 624, 626 may engage the resilient body.

As shown, the securing device 638 may be substantially similar to securing device 610 and includes a threaded portion 639 adapted to mate with a portion of the flange piece 622. The securing device 610 engages a shoulder portion of the opening 636 in the inferior attachment portion 632 to limit how far into the opening the securing device may travel. In the current embodiment, securing device 638 is longer than securing device 610. In other embodiments the securing device 638 may the same length or shorter than securing device 610. Any suitable means of securing the inferior attachment portion 602 to the flange piece 622 may be utilized. Further, the securing device 638 may be sized such that the securing device is recessed with respect to an inferior end 633 of the inferior attachment portion 632 when the superior attachment portion is secured to the flange piece 622.

FIG. 19 shows a cross-section of the vertebral stabilizer 600 fully assembled. Similar to the devices and systems described above, the vertebral stabilizer 600 is configured such that the resilient body 618 is compressed in both compression and extension. To this end, the flanges 614, 616, 624, and 626 are adapted to engage the resilient body 618 during compression. The flanges 606, 608, and 634 are adapted to engage the resilient body 618 during extension.

The foregoing embodiments may be provided individually or in a kit providing a variety of sizes of components as well as a variety of strengths for the central member. It some embodiments, the central members are color coded to provide the user with a convenient manner to readily determine the expected range of compressive and tensile loads the bumper is designed to dampen.

Although only a few exemplary embodiments have been described in detail above, those skilled in the art will readily appreciate that many modifications are possible in the exemplary embodiments without materially departing from the novel teachings and advantages of this disclosure. Accordingly, all such modifications and alternative are intended to be included within the scope of the invention as defined in the following claims. Those skilled in the art should also realize that such modifications and equivalent constructions or methods do not depart from the spirit and scope of the present disclosure, and that they may make various changes, substitutions, and alterations herein without departing from the spirit and scope of the present disclosure.

For example, the embodiments herein have described the central member as being compressed during both extension and compression. However, in other embodiments the central member is extended or stretched during both extension and compression. An example of such a central member is a central member having a hollow body such that the flanges would be disposed entirely within the central member, but where the ends of the central member have a diameter such that the flanges cannot pass through. Thus, as the flanges extended outward they engage the ends of the central member and stretch the central member. The central member provides resistance as its ends are separated. In that way, the embodiments described herein may be utilized to flex a central member during extension and compression, rather than compress the central member, without departing from the scope of the disclosure.

As another example, the flanges described above with respect to the various embodiments have been disclosed as being both single flanges and pairs of flanges. It should be noted, however, that these are simply exemplary embodiments. In other embodiments the flanges described above as a single flange are replaced by a plurality of flanges. Similarly, the flanges described in pairs above are replaced by a single flange or include additional flanges in other embodiments.

Further, the embodiments of the present disclosure may be adapted to work in combination or alone over multiple spinal levels and vertebral motion segments. Also, though the embodiments have been described with respect to the spine and, more particularly, to vertebral motion segments, the present disclosure has similar application to other motion segments and parts of the body.

It is further understood that all spatial references, such as "horizontal," "vertical," "top," "upper," "lower," "bottom," "left," "right," "cephalad," "caudal," "upper," and "lower," are for illustrative purposes only and can be varied within the scope of the disclosure. In the claims, means-plus-function clauses are intended to cover the elements described herein as performing the recited function and not only structural equivalents, but also equivalent elements.

We claim:

1. A system for flexibly stabilizing a first vertebra with respect to a second vertebra, the system comprising:
    a dynamic device comprising a first attachment portion, a second attachment portion, and a resilient member positioned between the first attachment portion and the second attachment portion, wherein the first and second attachment portions compress the resilient member when the first and second attachment portions move towards each other and compress the resilient member when the first and second attachment portions extend away from each other, wherein the first attachment portion includes a first flange adapted to transfer a first force to a first surface of the resilient member and wherein the second attachment portion includes a second flange adapted to transfer a second force to a second surface of the resilient member;
    a first fixation member for connecting the first attachment portion to the first vertebra;
    a second fixation member for connecting the second attachment portion to the second vertebra; and
    a first rod member connected to the first attachment portion, the first rod member having a third flange adapted to transfer a first tensile force to the second surface of the resilient member.

2. The system of claim 1, further including a second rod member connected to the second attachment portion, the second rod member having a fourth flange adapted to transfer a second tensile force to the first surface of the resilient member.

3. The system of claim 2, wherein the resilient member includes an opening adapted to receive the first and second rod members.

4. The system of claim 2, wherein the first and second rod members are flexible.

5. The system of claim 2, wherein the first rod member is connected to the first attachment portion by a first connector and the second rod member is connected to the second attachment portion by a second connector.

6. The system of claim 5, wherein the first connector is a first locking pin and the second connector is a second locking pin.

7. The system of claim 2, wherein the first attachment portion includes a first abutment surface adapted to engage the fourth flange to limit the movement of the first and second attachment portions towards each other.

8. The system of claim 7, wherein the second attachment portion includes a second abutment surface adapted to engage the third flange to limit the movement of the first and second attachment portions towards each other.

9. The system of claim 1, wherein the first attachment portion includes a first aperture adapted to receive the first fixation member to connect the dynamic device to the first vertebra.

10. The system of claim 1, wherein the first attachment member includes a first rod portion adapted for connecting to the first fixation member to connect the dynamic device to the first vertebra.

11. The system of claim 10, wherein the first rod portion is at least partially bent.

12. The system of claim 1, wherein the resilient member includes a spring.

13. The system of claim 12, wherein the spring is biased towards extension.

14. The system of claim 1, wherein the resilient member includes a plurality of perforations.

15. The system of claim 1, wherein the resilient member is made of PEEK.

16. The system of claim 1, wherein the first fixation member for connecting the dynamic device to the first vertebra is a pedicle screw.

17. The system of claim 16, wherein the pedicle screw is a multi-axial pedicle screw.

18. A dynamic device for use in a system for flexibly stabilizing a first vertebra with respect to a second vertebra, comprising:
a first attachment portion having a first flange and a second flange;
a first outer rod member connected to the first attachment portion, the first outer rod member having a third flange;
a second outer rod member connected to the first attachment portion, the second outer rod member having a fourth flange;
an inner rod member positioned between and slidably coupled with the first and second outer rod members, the inner rod member having a fifth flange;
a second attachment portion connected to the inner rod member, the second attachment portion having a sixth flange;
a resilient central member located at least partially between the first and second attachment portions, the resilient central member having an opening extending from a first side to a second side, the opening adapted to receive the first and second outer rod members and the inner rod member such that the first, second, and fifth flanges are positioned adjacent to the first side and the third, fourth, and sixth flanges are positioned adjacent to the second side.

19. The dynamic device of claim 18, further comprising a first bone fixation member for securing the first attachment portion to the first vertebra.

20. The dynamic device of claim 19, wherein the first bone fixation member extends through an opening in the first attachment portion.

21. The dynamic device of claim 18, wherein the first attachment portion, the first outer rod member, the second outer rod member, the inner rod member, the second attachment portion, and the resilient central member are formed from a biocompatible material suitable for in vivo implantation.

22. A system for dynamically stabilizing a first vertebra with respect to a second vertebra, the system comprising:
a first attachment portion for mating with a first bone fixation member;
a first engagement portion extending from the first attachment portion, the first engagement portion comprising a first flange member and a second flange member spaced from the first flange member;
a first rod member fixedly connected to the first engagement portion, the first rod member comprising a third flange member;
a second attachment portion for mating with a second bone fixation member;
a second engagement portion extending from the second attachment portion, the second engagement portion comprising a fourth flange member;
a second rod member fixedly connected to the second engagement portion, the second rod member comprising a fifth flange member;
a resilient member positioned between the first and second attachment portions and surrounding the first and second rod members, the resilient member having a first surface and an opposing second surface;
the first bone fixation member for securing the first attachment portion to the first vertebra; and
the second bone fixation member for securing the second attachment portion to the second vertebra;
wherein the system is movable between a neutral position, a compression position, and an extension position, wherein the first, second, and fourth flange members compress the resilient member in the compression position and wherein the third and fifth flange members compress the resilient member in the extension position; and
wherein the first and second attachment portions, the first and second engagement portions, the first and second rod members, and the resilient member are formed of a biomaterial suitable for in vivo implantation.

23. The system of claim 22, further comprising a third rod member fixedly connected to the first engagement portion, the third rod member spaced from the first rod member and comprising a sixth flange member.

24. The system of claim 23, wherein the third, fifth, and sixth flange members compress the resilient member in the extension position.

25. The system of claim 23, wherein the second rod is received between and slidably coupled with the first and third rods.

26. The system of claim 23, further comprising a first washer positioned between the first surface of the resilient member and the first, second, and fifth flange members.

27. The system of claim 26, further comprising a second washer positioned between the second surface of the resilient member and the third, fourth, and sixth flange members.

* * * * *